US008144191B2

(12) United States Patent
Kawanishi et al.

(10) Patent No.: US 8,144,191 B2
(45) Date of Patent: Mar. 27, 2012

(54) ENDOSCOPE VISUAL IMAGING AND PROCESSING APPARATUS

(75) Inventors: Tetsuya Kawanishi, Saitama (JP); Kazunori Abe, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 1511 days.

(21) Appl. No.: 11/370,992

(22) Filed: Mar. 9, 2006

(65) Prior Publication Data

US 2006/0203087 A1    Sep. 14, 2006

(30) Foreign Application Priority Data

Mar. 11, 2005   (JP) .............................. P. 2005-068800

(51) Int. Cl.
*G09G 5/00* (2006.01)
*G06F 3/14* (2006.01)
*A61B 1/04* (2006.01)
*A62B 1/04* (2006.01)
*H04N 5/222* (2006.01)

(52) U.S. Cl. ............. 348/65; 345/1.1; 345/2.2; 345/3.4; 345/1.3; 715/864; 348/77; 348/333.01

(58) Field of Classification Search ............ 345/1.1–3.4; 715/864
See application file for complete search history.

(56) References Cited

U.S. PATENT DOCUMENTS

| | | | |
|---|---|---|---|
| 5,871,439 A * | 2/1999 | Takahashi et al. ............ | 600/118 |
| 6,490,490 B1 | 12/2002 | Uchikubo et al. | |
| 6,491,628 B1 * | 12/2002 | Kobayashi ..................... | 600/168 |
| 6,992,694 B2 * | 1/2006 | Abe ................................ | 348/72 |
| 7,312,764 B2 * | 12/2007 | Driver et al. .................... | 345/1.1 |
| 2002/0057341 A1 * | 5/2002 | Tanaka .......................... | 348/143 |
| 2002/0057496 A1 * | 5/2002 | Kanai ........................... | 359/625 |
| 2002/0167460 A1 * | 11/2002 | Baudisch et al. .............. | 345/3.3 |
| 2006/0050090 A1 * | 3/2006 | Ahmed et al. ................ | 345/660 |

FOREIGN PATENT DOCUMENTS

| | | |
|---|---|---|
| JP | 1-99083 A | 4/1989 |
| JP | 2001-340292 A | 12/2001 |
| JP | 2004-267585 | * 9/2004 |

OTHER PUBLICATIONS

ForceWare Graphics Driver User's Guide Driver Release 60 for Windows, Jul. 2004, NVIDIA Corporation.*
Japanese Office Action, Apr. 19, 2010.

* cited by examiner

*Primary Examiner* — Lin Ye
*Assistant Examiner* — Chia-Wei A Chen
(74) *Attorney, Agent, or Firm* — Birch, Stewart, Kolasch & Birch, LLP

(57) ABSTRACT

An endoscope apparatus comprises: a scope comprising a solid imaging device; a processor unit which forms an observation image from signals emitted from the solid imaging device, the processor being connected to the scope; and a plurality of monitors each of which is connected to the processor unit, wherein a whole image of the observation image is displayed on at least one of said plurality of monitors, and a partial image of the observation image is enlarged and displayed on the other one(s) of said plurality of monitors.

3 Claims, 3 Drawing Sheets

ENDOSCOPE VISUAL IMAGING AND PROCESSING APPARATUS

BACKGROUND OF THE INVENTION

1. Field of the Invention

The present invention relates to an endoscope apparatus which is inserted into the body of a subject mainly for conducting an endoscopic surgery.

2. Description of the Related Art

An endoscope apparatus such as an electronic endoscope takes an image of a body to be observed which is illuminated by illumination light by using a CCD (charge coupled device), namely, a solid imaging device and gives a predetermined signal processing to the imaged observation image, thereby displaying the image on monitors. An endoscope apparatus is, therefore, provided with a scope loading a CCD and having an insertion portion, a processor unit having a light source for supplying illumination light, which gives a predetermined signal processing to an observation image taken by the CCD, and monitors for displaying the observation image which was subjected to signal processing in the processor unit. This type of endoscope apparatus can be used for not only in making a diagnosis or observation but also used in endoscopic surgery such as a cholecystectomy by an abdominoscope. An operator can carry out a procedure for an affected part by using treatment equipment such as forceps and scalpels while observing observation images displayed on monitors.

The above-described CCD takes a whole image of a wide area to the greatest possible extent so that an operator can recognize both the position of an affected part and that of treatment equipment. As described in JP-A-2001-340292, where an image of the vicinity of the affected part (interest area) is enlarged and displayed, the treatment equipment displayed on a whole image displaying the affected part and the treatment equipment may disappear from the screen. Therefore, the treatment equipment is not appropriately operated, thus, resulting in loss of a smooth and reliable operation of the equipment.

Under these circumstances, it has been demanded that a whole image and an enlarged image of an interest area be displayed at the same time. In response to such a demand, for example, JP-A-1-99083 has disclosed a system by which a whole image and an enlarged image are displayed on the screen of one monitor. More specifically, the screen of the monitor is divided to display a whole image and an enlarged image of an interest area.

In the above-described invention of JP-A-1-99083, a whole image and enlarged image of the interest area are displayed on the same monitor, which makes narrower the effective area for displaying the respective images, therefore, a problem is brought about that it is difficult of recognize the images.

Further, an enlarged image of an interest area is generated by electronically enlarging a whole image. The fact has been widely known that, in general, when an image is electronically enlarged, one pixel constituting an original image is given a certain processing (for example, interpolation) and displayed in a plurality of pixels, causing jaggy (zigzag) on a curved line or a diagonal line. Therefore, the contour of the image may be blurred to such an extent that an affected part cannot be accurately visualized for the details, depending on an enlargement ratio. In order to obtain a clear image of the interest area, it is preferable that no electronic enlargement processing is given at all or an enlargement ratio is kept to the lowest possible extent, thereby displaying an image on a monitor in such a way that processing given to respective pixels constituting the image taken by a CCD is suppressed as much as possible.

SUMMARY OF THE INVENTION

In this instance, an object of the present invention is to provide an endoscope apparatus which displays clearly a whole image and an enlarged image on a plurality of monitors at the same time.

The endoscope apparatus of the present invention comprises: a scope comprising a solid imaging device; a processor unit which forms an observation image from signals emitted from the solid imaging device, the processor being connected to the scope; and a plurality of monitors each of which is connected to the processor unit, wherein a whole image of the observation image is displayed on at least one of said plurality of monitors, and a partial image of the observation image is enlarged and displayed on the other one(s) of said plurality of monitors.

DETAILED DESCRIPTION OF THE INVENTION

A. Embodiment 1 of the Present Invention

Figure 1:
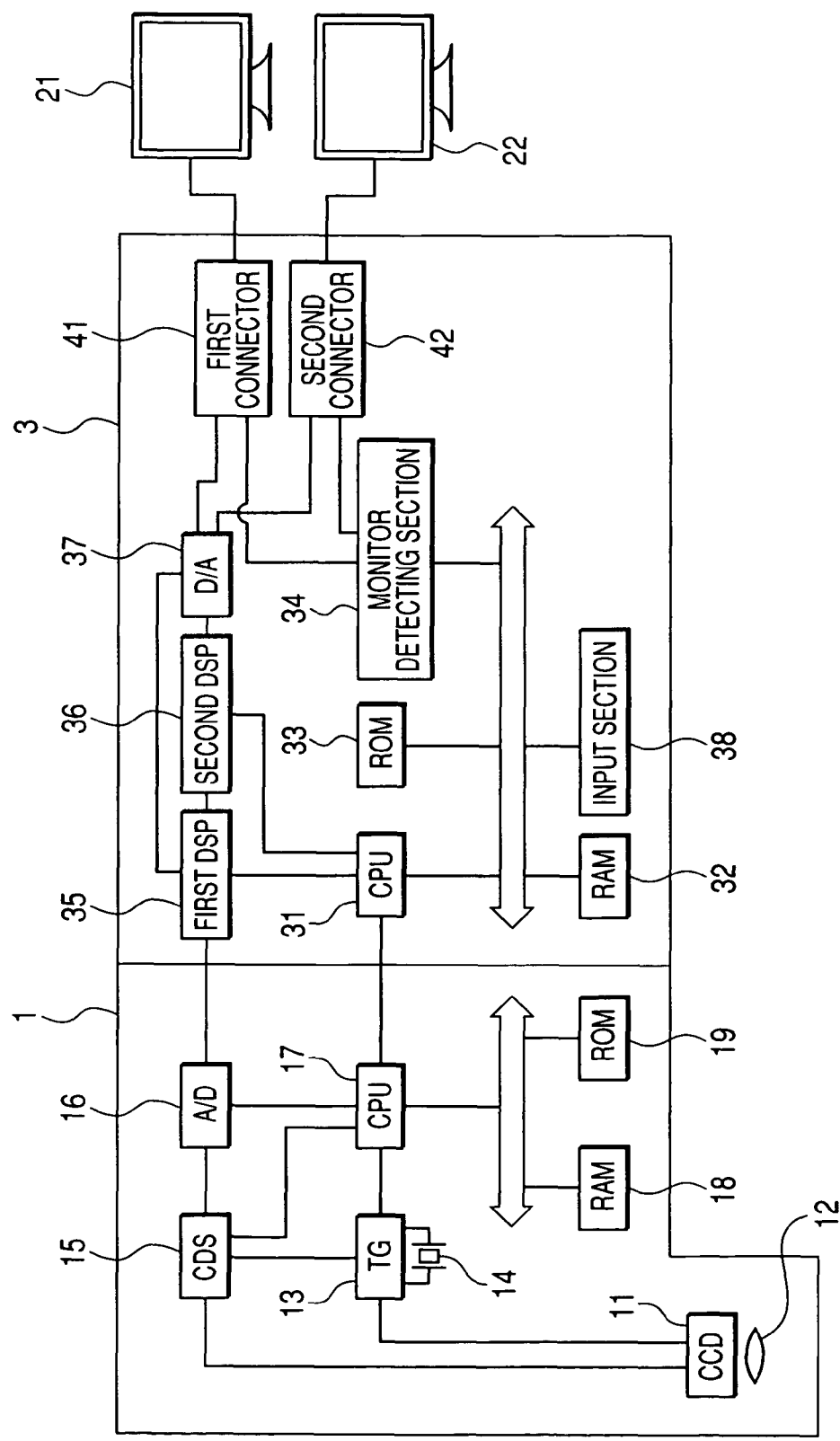
FIG. 1 is a view showing the whole constitution of an endoscope apparatus.

Hereinafter, a description is given for the embodiment 1 of the present invention. The endoscope apparatus of the present embodiment is constituted by a scope 1 and a processor unit 3, in which the scope 1 is connected to the processor unit 3. Further, a plurality of monitors are connected to the processor unit 3. FIG. 1 shows an example where two monitors are connected thereto.

The scope 1 is provided with a CCD 11 (solid imaging device), an objective lens 12, a TG (timing generator) 13, a quartz oscillator 14, a CDS (correlated double sampling) 15, an A/D (A/D converter: analog digital converter) 16, a CPU (central processing unit) 17, a RAM (random access memory) 18 and a ROM (read only memory) 19.

The CCD 11 is an imaging device which radiates to a body to be observed with illumination light supplied from a light source device (not illustrated), subjecting an optical image formed by the objective lens 12 to photoelectric conversion to generate video signals of an observation image. The TG 13 is a circuit for controlling the timing of driving the CCD 11 on the basis of a pulse generated by the quartz oscillator 14. The CCD 11, the driving of which is controlled by the TG 13, sweeps out an accumulated electrical charge at certain intervals, in which analog signals are converted to digital signals by the A/D 16 after signal processing and others are conducted for removing noise by the CDS 15 which conducts so-called correlated double sampling. Further, the CPU 17 develops the program recorded in ROM 19 on the RAM 18 for execution, thereby controlling the TG 13, the CDS 15 and the A/D 16.

In addition to the scope 1, a plurality of monitors are connected to the processor unit 3. Among these monitors, any one of them is a monitor for displaying a whole image that is taken by the CCD 11, and the rest of the monitors are monitors for enlarging and displaying an image of a part of the interest area of the whole image (partial image). These monitors may be available in any given size and resolution. FIG. 1 shows an example in which two monitors are connected to the processor unit 3, namely, the monitor for displaying a whole image is designated as a whole monitor 22 and that for displaying an enlarged partial image is designated as an enlargement monitor 21. The partial image which has been electronically enlarged is displayed on the screen of the enlargement monitor 21. Further, the enlargement monitor 21 and the whole monitor 22 may include digital display monitors such as an LCD (liquid crystal display) and analog display monitors such as a CRT (cathode ray tube). Hereinafter, a description is given for the embodiment employing digital display monitors.

Next, a description is given for the processor unit 3. The processor unit 3 is provided and constituted by a CPU 31, a RAM 32, a ROM 33, a monitor detecting section 34, a first DSP (digital signal processor) 35, a second DSP 36, a D/A (D/A converter: digital analog converter) 37, an input section 38, a first connector 41 and a second connector 42.

The CPU 31 controls the operation of the processor unit 3 to develop the program accommodated in ROM 33 on the RAM 32 for execution. Further, the monitor detecting section 34 is able to obtain information on resolution of the enlargement monitor 21 and that of the whole monitor 22 connected to the processor unit 3 via the first connector 41 and the second connector 42 and to output the information to the CPU 31.

The first DSP 35 is connected to the A/D 16 of the scope 1 to give various digital processings such as amplification, white balance and gamma correction to video signals of the observation image converted to digital signals at the A/D 16, thereby forming a whole image to be displayed on a monitor. Then, the second DSP 36 specifies a partial image in a whole image formed in the first DSP 35 by clipping and selecting a range to a part of the whole image. Further, when the thus specified partial image is electronically enlarged, the second DSP 36 conducts the electronic enlargement processing. In this instance, in the second DSP 36, a central part of the whole image is to be initially specified as a partial image. More specifically, a central part of the observation image is to be given as a center of the displayed image. Further, where a partial image of other parts in place of the central part is specified, an input section 38 is operated to specify the position of the partial image in the whole image.

A whole image formed at the first DSP 35 and a partial image specified at the second DSP 36 and electronically enlarged are respectively connected to a D/A 37 and converted to analog signals by the D/A 37. Thereafter, the partial image is enlarged via the first connector 41 and displayed on the enlargement monitor 21, whereas the whole image is displayed on the whole monitor 22 via the second connector 42. Further, where the first connector 41 and the second connector 42 are able to output digital signals, the D/A 37 is not necessary and these images are output as digital signals on the enlargement monitor 21 and the whole monitor 22. In addition, since two monitors are connected to the processor unit 3 in FIG. 1, two connectors, or the first connector 41 and the second connector 42, are required. However, where three or more monitors are connected to the processor unit 3, the processor unit 3 is equipped with the corresponding number of connectors.

According to the above-described constitution, a whole image taken by the CCD 11 can be displayed on one monitor (whole monitor 22) among a plurality of monitors, and an enlarged image which is a part of the interest area of the whole image can be displayed on other monitors (enlargement monitor 21). A whole image and an enlarged partial image can be displayed at the same time, thereby preventing a deteriorating operation of treatment equipment and providing a smooth and reliable operation. Further, the whole image and the enlarged partial image can, respectively, be displayed on monitors, thereby preventing an effective display area from being narrowed.

B. Embodiment 2 of the Present Invention

Next, a description is given for the embodiment 2 of the present invention. As with the embodiment 1, in the embodiment 2, among a plurality of monitors, a whole image is displayed on one monitor and an enlarged partial image is displayed on the rest of monitors. In this instance, it is preferable that the monitor displaying a whole image has a resolution greater than the pixel number of the CCD 11. In order to display an enlarged partial image at a high quality, a plurality of monitors connected to the processor unit 3 have the respective resolutions. The monitor having the highest resolution is used as a monitor for displaying a whole image, whereas the rest of the monitors are used for displaying an enlarged partial image. Hereinafter, the resolution of the monitor for displaying a whole image is equal to or greater than the pixel number of the CCD 11, and the resolution of the monitor(s) for displaying an enlarged partial image is equal to or smaller than the pixel number of the CCD 11.

The resolution of a monitor displaying a whole image is greater than the pixel number, therefore, it is possible to display one pixel of a whole image taken by the CCD 11 as one pixel of the monitor. Thus, no electronic enlargement processing is necessary at all for any pixel taken by the CCD 11, thereby making it possible to display an image taken by the CCD 11 as it is and also to clearly display a whole image at a high quality on the screen of the monitor.

A partial image can be enlarged and displayed by giving electronic enlargement processing to the partial image, however, as the enlargement ratio becomes higher, the quality of an image becomes lower. Therefore, when an enlarged image of a partial image is displayed, the image is not electronically enlarged or monitors having a lower resolution are allocated as monitors for enlarging and displaying the partial image so as to keep the enlargement ratio to the lowest possible extent, even if the image is electronically enlarged and displayed. Since a monitor having a lower resolution has a small pixel number, it is possible to display one pixel of a partial image in the specified interest area in a form close to one pixel of the monitor. In this instance, if there is not a substantial difference in the size between a monitor for displaying a whole image and that for displaying a partial image, the one-pixel size constituting the partial image in itself can be displayed in a larger size. Therefore, the partial image without giving electronic enlargement processing can be enlarged and displayed, thereby making it possible to display an enlarged image at a high quality with the resolution as it is.

In this instance, where a ratio of a partial image clipped from a whole image to the whole image equals a ratio of the resolution of a monitor displaying the partial image enlarged to that of a monitor displaying the whole image, the size of a unit pixel can be enlarged without giving electronic enlargement processing at all. Therefore, it is possible to enlarge and display on monitors the partial image without deterioration in image quality. However, the ratio is not always the same depending on an area of the specified partial image. In this instance, the partial image can be enlarged and displayed so that the enlargement ratio of electronic enlargement processing given to the partial image can be suppressed not only by use of electronic enlargement processing, but by use of an enlargement display with a monitor having a low resolution and electronic enlargement processing. Therefore, the partial image can be enlarged and displayed at a high quality.

Figure 2:
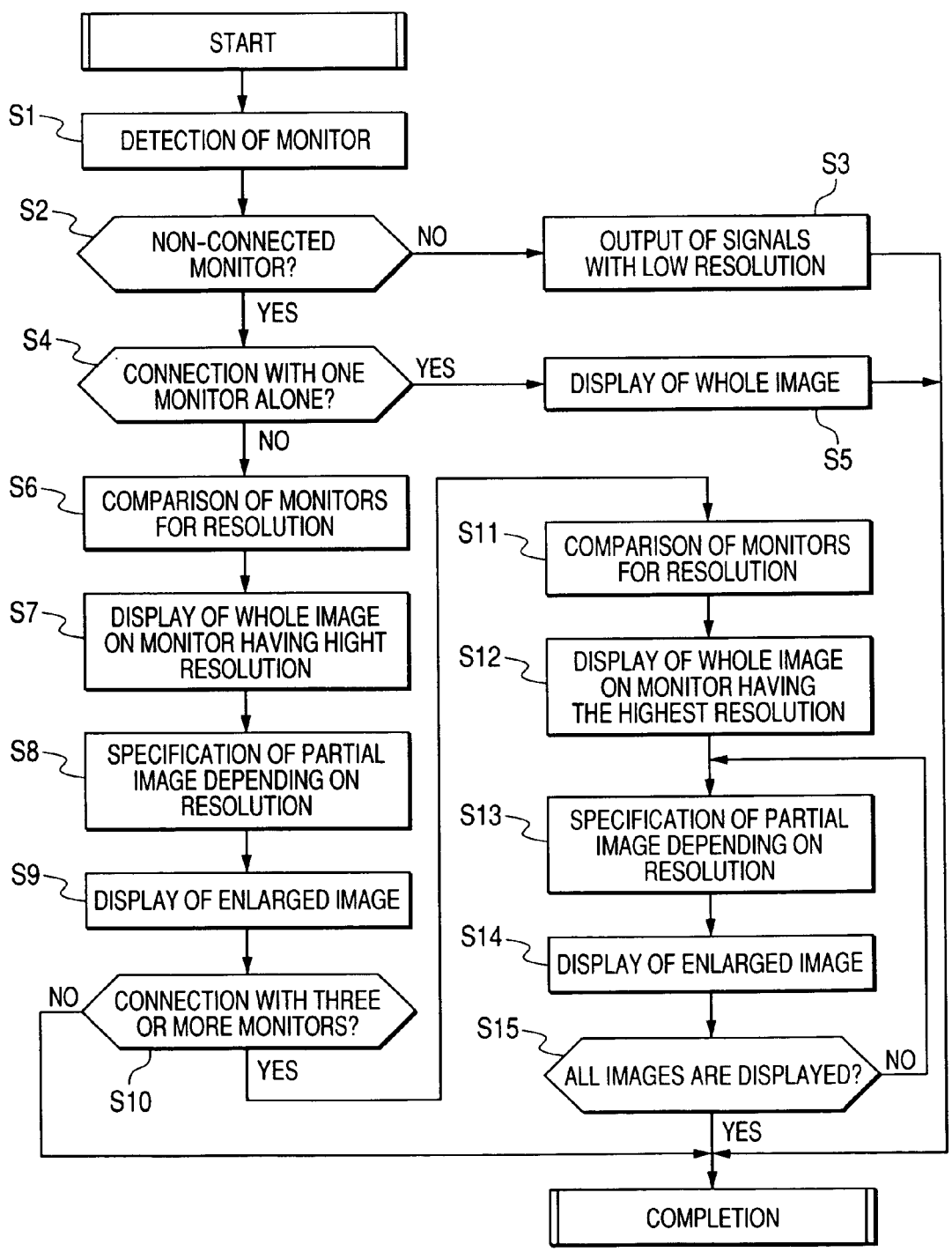
FIG. 2 is a flowchart showing the processing.

Hereinafter, a description is given to a concrete example with reference to the flowchart of FIG. 2. As with the embodiment 1, of two monitors, one monitor is used as a whole monitor 22 for displaying a whole image, and the other is used as an enlargement monitor 21 for displaying a partial image. As described above, the resolution of the enlargement monitor 21 is to be lower than that of the whole monitor 22, and the CCD 11 has a pixel number equal to or lower than the resolution of the whole monitor 21 but has a pixel number equal to or greater than the resolution of the enlargement monitor 22. Further, it is preferable that the screen size is substantially similar between the enlargement monitor and the whole monitor, although such a condition is met that the screen-size ratio of the enlargement monitor 21 to the whole monitor 22 is equal to or greater than the ratio of the partial image to the whole image.

First, a monitor detecting section 34 detects the number of monitors connected to a processor unit 3, to obtain information on the resolution of the enlargement monitor 21 and of the whole monitor 22 via a first connector 41 and a second connector 42 (step S1). In this instance, where at least one monitor is connected to the processor unit 3, the step proceeds to a step S4 to be described later. However, where no monitor is connected thereto (step S2), other peripheral devices such as a copy device may be connected (step S3), therefore, a signal of the lowest resolution that can be output from the processor unit 3 is outputted from the processor unit 3 to complete the step. Further, where only one monitor is connected to the processor unit 3 (step S4), a whole image is displayed to complete the processing, because the monitor is required to display the whole image (step S5).

Where two or more monitors are connected to the processor unit 3, the processor unit 3 compares these monitors for the resolution (step S6). In FIG. 1, since two monitors, namely, an enlargement monitor 21 and a whole monitor 22, are connected to the processor unit 3, the processor unit 3 compares these monitors for the resolution. In this instance, of these two monitors, the enlargement monitor 21 is lower in resolution than the whole monitor 22, therefore, the processor unit 3 controls these monitors so that a whole image is therefore to be displayed on the whole monitor 22 having a high resolution (step S7). In contrast, a partial image is specified for the extent from the whole image, depending on the resolution of the monitor (step S8) and displayed on the enlargement monitor 21 having a low resolution (step S9).

Where a whole monitor 22 is equal in aspect ratio to an enlargement monitor 21, the display pixel number of the monitor 21 is designated as P1, the screen size is D1, the display pixel number of the whole monitor 22 is P2 and the screen size is D2. In this instance, a partial image displayed on the enlargement monitor 21 is to be enlarged by a factor of (P2/P1)×(D1/D2) in relation to a whole image displayed on the whole monitor 22. Therefore, the smaller the display pixel number of the enlargement monitor 21 (P1) becomes in relation to the display pixel number of the whole monitor 22 (P2), or the greater the screen size of the enlargement monitor 21 (D1) becomes in relation to the screen size of the whole monitor 22 (D2), the grater the partial image will be enlarged and displayed accordingly.

It is, therefore, possible to display on the whole monitor 22 a whole image covering a wide area including an affected part and treatment equipment at a high quality and also to enlarge and display on the monitor 21 a clear partial image which has not been electronically enlarged at all, when the affected part is checked elaborately. Further, there is a case where the partial image may be electronically enlarged to some extent, depending on the enlargement ratio. In this case, the enlargement ratio can also be kept low, thereby making it possible to display the enlarged image at a high quality.

A description is given for a case where the pixel number of the CCD 11 is 1280×960 pixels, the resolution of the whole monitor 22 is SXGA (super extended graphic array: 1280× 1024 pixels), the resolution of the enlargement monitor 21 is VGA (video graphic array: 640×480 pixels) and ¼ area of the whole image is clipped as an example. It is preferable to clip an area of 20 to 80%.

Figure 3:
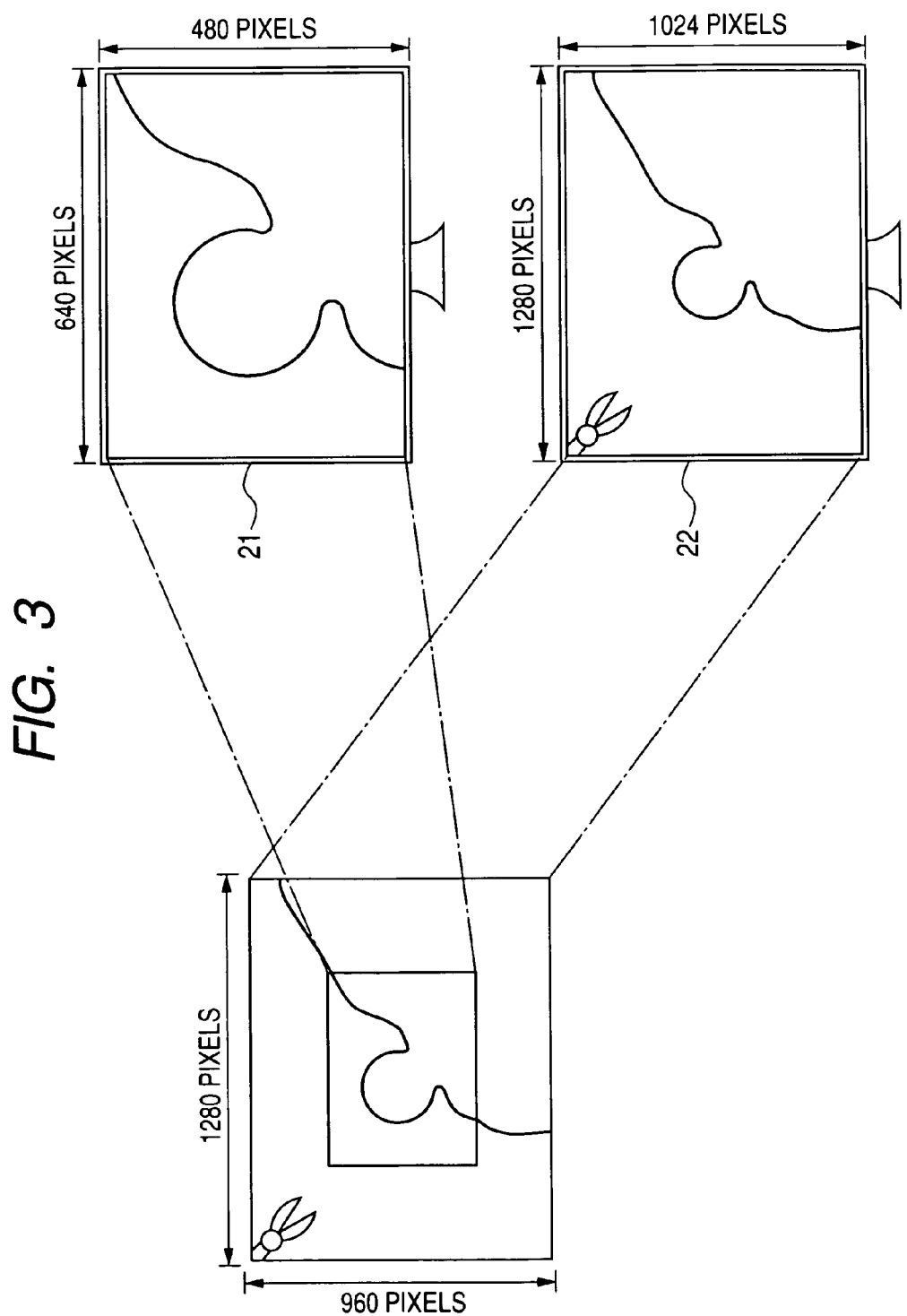
FIG. 3 is a view showing images displayed on the respective monitors.

In this instance, as shown in FIG. 3, a whole image is displayed on the whole monitor 22 having a higher resolution than the pixel number of the CCD 11 so that one pixel of the CCD 11 can constitute one pixel of the whole monitor 22. Therefore, the whole image is displayed on the whole monitor 22 without giving electronic enlargement processing. In contrast, since the pixel number of the enlargement monitor 21 for enlarging and displaying a partial image corresponds to ¼ of the pixel number of the CCD 11, the pixel number constituting the partial image equals the pixel number of the enlargement monitor 21. Further, one pixel of the CCD 11 can be displayed as one pixel of the enlargement monitor 21, thereby making it possible to enlarge and display a partial image as it is, without giving electronic enlargement processing at all. Therefore, the partial image can be enlarged and displayed at a high quality, with the resolution sensitivity kept as it is. More specifically, the image does not deteriorate in quality because only the unit pixel is enlarged in size but one pixel of the CCD 11 can be displayed as one pixel as before.

As a matter of course, there is a case where the pixel number constituting a partial image does not equal the pixel number of the enlargement monitor 21, depending on a range of the partial image cut out from the whole image. In this instance, an enlargement monitor 21 having a lower resolution than a whole monitor 22 is used to electronically enlarge a partial image, thereby making it possible to enlarge and display the partial image, while reducing the enlargement ratio of electronic enlargement processing. Therefore, it is possible to display an enlarged partial image at a high quality on a monitor.

Further, where it is desired to display a partial image on a greatly enlarged scale, a monitor may be provided in accordance with the size of the partial image. A monitor capable of enlarging and displaying an image to a certain extent may be provided to display the image after the partial image displayed on the monitor is further electronically enlarged. For example, if a monitor having QVGA (quarter video graphic array: 320×240 pixels) is provided for an video signal taken by the CCD 11 having 1280×960 pixels, an image can be enlarged 16 times for display. However, the monitor having QVGA size is in principle very small in dimensions, which poses a great problem of visibility to an operator. Therefore, as described above, if the enlargement monitor 21 having VGA resolution is provided to electronically enlarge 4 times a partial image having the resolution of ¼ as compared with the whole image, the image can be enlarged 16 times.

As described above, where a partial image is electronically enlarged, an image containing some jagging to some extent is displayed. However, there is in principle a great difference in sharpness between a whole image electronically enlarged 16 times and a partial image which is a part of the whole image which has been electronically enlarged 4 times. In other words, there is a great difference in the degree of jaggy between a whole image electronically enlarged 16 times displayed on the enlargement monitor 21 and an image formed by electronically enlarging 4 times a partial image which has not been electronically enlarged at all as described above. There is also a remarkable difference in blurred contour between them. Therefore, even if electronic enlargement processing was carried out, there is not such a large problem with regard to visibility for an operator, or resolution sensitivity as long as the enlargement ratio can be kept to the lowest limit.

Further, an operator is able to display an image at any given enlargement ratio by giving electronic shrinking processing or electronic enlargement processing to a partial image, thereby increasing the degree of freedom.

As described above, where two monitors are connected to the processor unit 3, an enlarged partial image is displayed on the enlargement monitor 21 and a whole image is displayed on the whole monitor 22, making it possible to display the whole image and the enlarged image of an interest area at the same time and also display them on the respective monitors, thereby removing a problem that an effective display area is narrowed. Further, the processor unit 3 controls the monitors so that a whole image is displayed on a high resolution monitor and a partial image is displayed on a low resolution monitor, thereby displaying the whole image and the partial image which has not been electronically enlarged or has been electronically enlarged at a low enlargement ratio quite naturally, if any, on the respective monitors. In addition, where a partial image is enlarged and displayed, the electronic enlargement processing can be suppressed to the lowest limit, therefore, an image quite close to that taken by the CCD 11, and an operator can visualize the whole image displayed on the whole display monitor 22 and the partial image displayed on the enlargement monitor 21, respectively, at the same time and in a quite clear fashion, thereby preventing deterioration in operability and loss in smoothness of operation.

Next, a description is given for a case where three or more monitors are connected. Where two monitors are connected to the processor unit 3 (step S10) as described above, a whole image is displayed on a high resolution monitor, while an enlarged image is displayed on a low resolution monitor, and the processing is then completed. Where three or more monitors are connected to the processor unit 3, all the monitors connected to the processor unit 3 are detected for resolution (step S11). Then, the processor unit 3 controls the monitors so that, of all the monitors detected for resolution, a whole image is displayed on a monitor having the highest resolution (step S12), a partial image is specified for other monitors in accordance with the resolution of each monitor (step S13), and the specified partial image is displayed on the screen of each monitor (step S14).

For example, where in addition to the above-described whole monitor 22 and the enlargement monitor 21, a monitor (hereinafter referred to as a third monitor) having a resolution of XGA (1024×768 pixels) and a screen size substantially similar to that of the whole monitor 22 is connected to the processor unit 3, the processor unit 3 controls the monitors so that the enlargement monitor 21 of a whole image is displayed on the whole monitor 22 having the highest resolution by comparing the whole monitor 22, the enlargement monitor 21 and the third monitor for the resolution. Then, a partial image is specified from the whole image (1280×960 pixels) according to the resolution (VGA: 640×480 pixels) of the enlargement monitor 21 and the resolution (XGA: 1024×768 pixels) of the third monitor, and the specified partial image is displayed on the screen of each monitor. In this instance, the unit pixel of the third monitor is 1.56 times and that of the enlargement monitor 21 is 4 times greater than that of the whole image. Since a wide partial image is specified for the third monitor having a high resolution, the partial image is enlarged and displayed at a small scale. Since a narrow partial image is specified in the enlargement monitor 21 having a low resolution, the partial image is enlarged and displayed at a large scale.

The above processing is given to all the monitors connected to the processor unit 3 until an image is displayed (step S15) and completed when the image is displayed on all the monitors.

As described above, where three or more monitors are connected to the processor unit 3, it is possible to display a whole image and two enlarged images of the interest area at the same time in an easily visible way. Then, a whole image is displayed on the monitor having the highest resolution, a partial image is enlarged and displayed at a small scale on the monitor having a higher resolution among other monitors and a partial image is enlarged and displayed at a large scale on the monitor having a low resolution. These images can be displayed at the same time, and also quite natural images which have not been electronically enlarged or which have been electronically displayed at a low enlargement ratio on all the monitors can be displayed. Therefore, a partial image covering only an affected part, or, for example, a partial image covering the affected part and a part of treatment equipment, may be displayed at the same time, together with a wide whole image covering the treatment equipment and the affected part, thereby increasing reliability of operation. As a matter of course, an electronically enlarged partial image may be displayed, however, the image close to that taken by the CCD 11 can be enlarged and displayed, since the electronic enlargement ratio can be suppressed to the lowest limit.

In addition, it is described that the CCD 11 has a pixel number of 1280×960. By use of a CCD having a larger pixel number a clear image of a wider range can be obtained. In this instance, a monitor having a high resolution such as UXGA (ultra extreme graphics array: 1600×1200 pixels) is applied as a monitor for displaying a whole image.

The endoscope apparatus of the present invention is able to display a whole image and an enlarged image at a high quality on a plurality of monitors at the same time.

The entire disclosure of each and every foreign patent application from which the benefit of foreign priority has been claimed in the present application is incorporated herein by reference, as if fully set forth.

What is claimed is:

1. An endoscope apparatus comprising:
   an endoscope comprising a solid imaging device;
   a processor unit which forms an observation image from signals emitted from the solid imaging device, the processor being connected to the endoscope; and
   one or a plurality of monitors each of which is connected to the processor unit, wherein the processor unit detects the number of connected monitors thereto, when the connected monitor is plural, a whole image of the observation image is controlled to be displayed on at least one of said plurality of monitors in the plurality of connected monitors, and a partial image of the observation image is enlarged and displayed on the other one(s) of said plurality of monitors, and
   when the connected monitor is single, the monitor is controlled to display the whole image of the observation image
   wherein if the processor unit detects that the number of connected monitors is plural, the monitors have respective different resolutions,
   the processor unit obtains a resolution of each of the monitors, and controls the monitors so that a whole image of the observation image can be displayed on a high resolution monitor having the highest resolution and a partial image of the observation image can be displayed on at least one low resolution monitor having lower resolution than the highest resolution, and each one of pixels of at least one of said at least one low resolution monitor can be displayed so as to correspond to each one of pixels corresponding to the partial image of the solid imaging device, by which the partial image can be enlarged and displayed on said at least one of the low resolution monitor, wherein the pixel number of the highest resolution monitor is greater than the pixel number of the solid imaging device, the pixel number of the low resolution monitor is equal to or smaller than the pixel number of the solid imaging device, a pixel size of the low resolution monitor is larger than a pixel size of the highest resolution monitor, and the partial image of the observation image can be displayed on the low resolution monitor without electronic enlargement processing.

2. The endoscope apparatus according to claim 1, wherein the high resolution monitor and said at least one low resolution monitor have the same screen size.

3. The endoscope apparatus according to claim 1, wherein the partial image is further electronically enlarged and displayed on at least one of said at least one low resolution monitors.

* * * * *